United States Patent
Butler et al.

(10) Patent No.: US 8,241,358 B2
(45) Date of Patent: Aug. 14, 2012

(54) RADIALLY EXPANDABLE SPINAL INTERBODY DEVICE AND IMPLANTATION TOOL

(75) Inventors: Michael S. Butler, St. Charles, IL (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 676 days.

(21) Appl. No.: 12/079,737

(22) Filed: Mar. 28, 2008

(65) Prior Publication Data

US 2008/0243255 A1     Oct. 2, 2008

Related U.S. Application Data

(60) Provisional application No. 60/920,766, filed on Mar. 29, 2007.

(51) Int. Cl.
    *A61F 2/44*           (2006.01)
(52) U.S. Cl. .................................... 623/17.11
(58) Field of Classification Search .... 623/17.11–17.16; 606/246–279
    See application file for complete search history.

(56) References Cited

U.S. PATENT DOCUMENTS

| | | | |
|---|---|---|---|
| 7,018,413 B2 | 3/2006 | Kruger | |
| 2004/0073312 A1* | 4/2004 | Eisermann et al. | 623/17.14 |
| 2004/0249466 A1* | 12/2004 | Liu et al. | 623/17.16 |
| 2005/0043800 A1* | 2/2005 | Paul et al. | 623/17.15 |
| 2005/0113920 A1* | 5/2005 | Foley et al. | 623/17.11 |
| 2006/0089642 A1 | 4/2006 | Diaz et al. | |
| 2006/0142858 A1* | 6/2006 | Colleran et al. | 623/17.11 |
| 2006/0224241 A1 | 10/2006 | Butler et al. | |

OTHER PUBLICATIONS

International Preliminary Report on Patentability and Written Opinion for PCT/US2008/004050, issued Sep. 29, 2009, 7 pages.
International Search Report and Written Opinion for PCT/US08/04050, mailed Jul. 21, 2008, 10 pages.

\* cited by examiner

*Primary Examiner* — Eduardo C Robert
*Assistant Examiner* — Nicholas Plionis
(74) *Attorney, Agent, or Firm* — Foley & Lardner LLP

(57) ABSTRACT

A radially expandable spinal interbody device for implantation between adjacent vertebrae of a spine is deliverable to an implant area in a radially collapsed state having minimum radial dimensions and once positioned is then radially expandable through and up to maximum radial dimensions. The expanded radially expandable spinal interbody device is configured to closely mimic the anatomical configuration of a vertebral face. The radially expandable spinal interbody device is formed of arced, pivoting linkages that allow transfiguration from the radially collapsed minimum radial dimensions through and up to the radially expanded maximum radial dimensions once deployed at the implant site (i.e. between adjacent vertebrae). The pivoting linkages have ends with locking features that inhibit or prevent overextension of the linkages. In one form of the locking features, one end of the linkage includes lobes that form a pocket while the other end of the linkage includes a projection that is adapted to be received in the pocket of the lobes of an adjacent linkage. A kit is also provided including a tool for the implantation and deployment of the spinal interbody device into an intervertebral space.

19 Claims, 6 Drawing Sheets

RADIALLY EXPANDABLE SPINAL INTERBODY DEVICE AND IMPLANTATION TOOL

RELATED APPLICATIONS

This patent application claims the benefit of and/or priority to U.S. Provisional Patent Application Ser. No. 60/920,766 filed Mar. 29, 2007, entitled "Expandable Spinal Interbody Device and Implantation Tool" the entire contents of which is specifically incorporated herein by reference.

BACKGROUND OF THE INVENTION

1. Field of the Invention

The present invention relates to spinal interbody devices for implantation between a pair of adjacent vertebrae for providing support to the adjacent vertebrae for fusion thereof and, more particularly, to expandable interbody devices for implantation between a pair of adjacent vertebrae for providing support to the adjacent vertebrae for fusion thereof.

2. Background Information

The disc between vertebrae of a human spine may become damaged due to disease, injury, stress, deterioration because of age or otherwise, or due to a congenital defect. In some instances vertebrae may become compressed against a disc or otherwise become damaged. The spine may thereby become mis-aligned. In these and other cases the vertebrae can become too closely spaced anteriorly which causes an undesired abnormal curvature of the spine with respect to lordosis or kyphosis. Other deformations and/or problems may occur.

In these cases and more, spinal fusion surgery may be utilized to join or fuse two or more vertebrae together. Fusion surgeries typically require the use of bone graft to facilitate fusion. This involves taking small amounts of bone from the patient's pelvic bone (autograft), or from a donor (allograft), and then packing it between the vertebrae in order to "fuse" them together. This bone graft is typically packed into a biomechanical spacer implant, spinal prosthesis or interbody device, which will take the place of the intervertebral disc which is entirely removed in the surgical process. Spinal fusion surgery is a common treatment for such spinal disorders as spondylolisthesis, scoliosis, severe disc degeneration, or spinal fractures. Three common fusion surgeries are 1) Posterior Lumbar Interbody Fusion or PLIF; 2) Anterior Lumbar Interbody Fusion or ALIF; and 3) Transforaminal Lumbar Interbody Fusion (TLIF).

In the PLIF technique, the vertebrae are reached through an incision in the patient's back (posterior). The PLIF procedure involves three basic steps. One is pre-operative planning and templating including use of MRI and CAT scans to determine what size implant(s) the patient needs. Two is preparing the disc space. Depending on the number of levels to be fused, a 3-6 inch incision is made in the patient's back and the spinal muscles are retracted (or separated) to allow access to the vertebral disc. The surgeon then removes some or all of the affected disc and surrounding tissue. Third is insertion of the implant(s). Once the disc space is prepared, bone graft, allograft or BMP with a biomechanical spacer implant, is inserted into the disc space to promote fusion between the vertebrae. Additional instrumentation (such as rods or screws) may also be used to further stabilize the spine.

The TLIF technique is a refinement of the PLIF procedure and is used as a surgical treatment for conditions typically affecting the lumbar spine. The TLIF technique involves approaching the spine in a similar manner as the PLIF approach but more from the side of the spinal canal through a midline incision in the patient's back. This approach greatly reduces the amount of surgical muscle dissection and minimizes the nerve manipulation required to access the vertebrae, discs and nerves. The TLIF approach allows for minimal access and endoscopic techniques to be used for spinal fusion. Disc material is removed from the spine and replaced with bone graft (along with cages, screws, or rods if necessary) inserted into the disc space. The instrumentation helps facilitate fusion while adding strength and stability to the spine.

The ALIF procedure is similar to PLIF procedure however, the ALIF procedure is done from the front (anterior) of the body, usually through a 3-5 inch incision in the lower left lower abdominal area. This incision may involve cutting through, and later repairing, the muscles in the lower abdomen. This technique also lends itself to a mini open approach that preserves the muscles and allows access to the front of the spine through a very small incision and use of endoscopic technology. This approach maintains abdominal muscle strength and function. It is therefore oftentimes used to fuse the L5-S1 disc space. As such, it can be appreciated that the smaller the interbody device the better.

When interbody devices are used, it is desirable for them to engage as much surface of the bone of the vertebrae as possible to provide support to the vertebral bone and to thereby reduce the likelihood of subsidence of the device into the bone resulting from contact pressure of the interbody device against bone surfaces. Subsidence can occur since part of the bone is somewhat spongy in nature, especially near the centers of the adjacent vertebrae.

The structure of interbody devices mainly functions to support the two adjacent vertebral surfaces, unless the interbody device is also used as a fusion cage within or around which to pack bone fusion material. Because it is also desirable in such structures to maintain weight and volume as low as possible in order to make the device more compatible with the body, it is also desirable to make the interbody device as small and lightweight as possible, while still maintaining strength.

Accordingly, there presently exists a need for improved interbody devices.

SUMMARY OF THE INVENTION

The present invention is a radially expandable spinal interbody device for implantation between adjacent vertebrae of a spine. The radially expandable interbody device is deliverable to an implant area in a radially collapsed state having minimum radial dimensions and once positioned is then radially expandable through and up to maximum radial dimensions. The expanded radially expandable spinal interbody device is configured to closely mimic the anatomical configuration of a vertebral face.

The radially expandable spinal interbody device is formed of arced, pivoting linkages that allow transfiguration from the radially collapsed minimum radial dimensions through and up to the radially expanded maximum radial dimensions once deployed at the implant site (i.e. between adjacent vertebrae). The pivoting linkages have ends with locking features that inhibit or prevent overextension of the linkages. In one form of the locking features, one end of the linkage includes lobes that form a pocket while the other end of the linkage includes a projection that is adapted to be received in the pocket of the lobes of an adjacent linkage.

In one form, the radially expandable spinal interbody device utilizes two like linkages that are pivotally connected to one another at opposite ends thereof. Each linkage is preferably, but not necessarily, formed of two pivotally connected arced links. The links each have serrations or teeth on upper and lower surfaces. The links are connected via pivot pins that also provide markers when formed of a radio opaque material such as tantalum.

The radially expandable spinal interbody device is made from a bio-compatible material such as titanium, a titanium alloy, stainless steel, other metal, polymer, composite, ceramic or a combination thereof as appropriate. The radially expandable interbody device 10 is preferably, but not necessarily, used as a lumbar interbody device and/or for use in ALIF surgery.

A surgical tool is provided for positioning and deploying the radially expandable interbody device/implant. The surgical tool has a positioning portion adapted to releasably attach to the radially expandable interbody device and a deployment portion movably retained by the positioning portion and adapted to deploy the radially expandable interbody device. The deployment portion is also adapted to introduce bone graft, BMP or the like into the radially expandable interbody device.

Releasable attachment to the radially expandable interbody device is accomplished in one form through multi-directional installation threads of a bore of each link. Since each link includes a threaded bore, various rotational orientations may be achieved during implantation.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A full dissertation of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN EMBODIMENT OF THE INVENTION

Referring to the Figures and in particular FIGS. 1-6, there is depicted an exemplary embodiment of a radially expandable interbody device, spinal prosthesis or the like generally designated 10 fashioned in accordance with the present principles. The radially expandable interbody device 10 is configured to be delivered to an implant site in a radially collapsed state or with radially minimal dimensions 200 (see, e.g., FIG. 8) and then radially expanded or with radially maximum dimensions 300 at the implant site (see, e.g., FIG. 9) hence the term expandable or dynamic. In this manner, the radially expandable interbody device 10 may be delivered to the implant site through a small delivery area when in the radially collapsed state and then easily radially expanded when implanted. The radially expandable interbody device 10 may be fashioned from a biocompatible material such as titanium, a titanium alloy, stainless steel, other metal, polymer, composite, ceramic and/or any combination thereof. The radially expandable interbody device 10 is preferably, but not necessarily, used as a lumbar interbody device and/or for use in an ALIF surgery.

Figure 1:
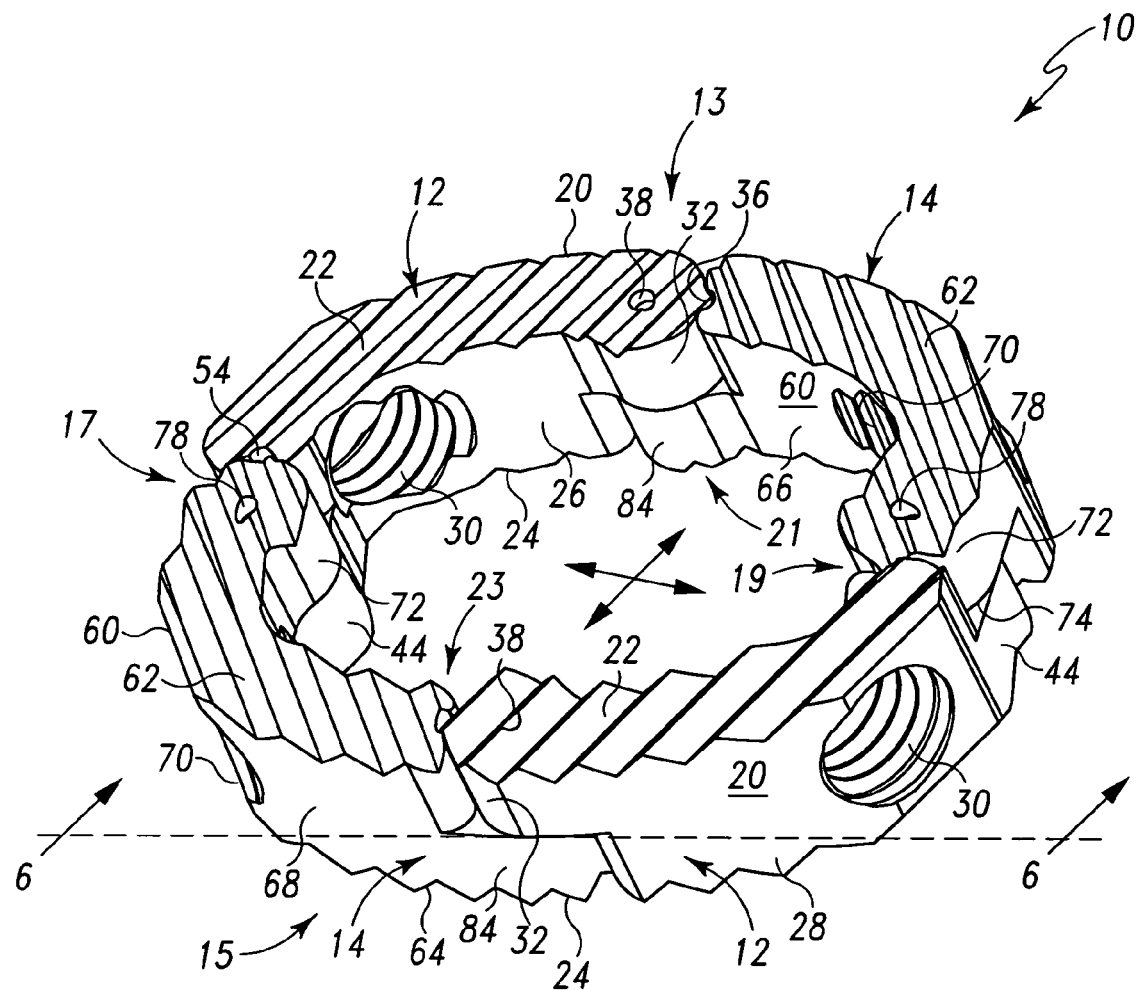
FIG. 1 is a perspective view of an exemplary embodiment of a radially expandable spinal interbody device fashioned in accordance with the present principles.
Figure 2:
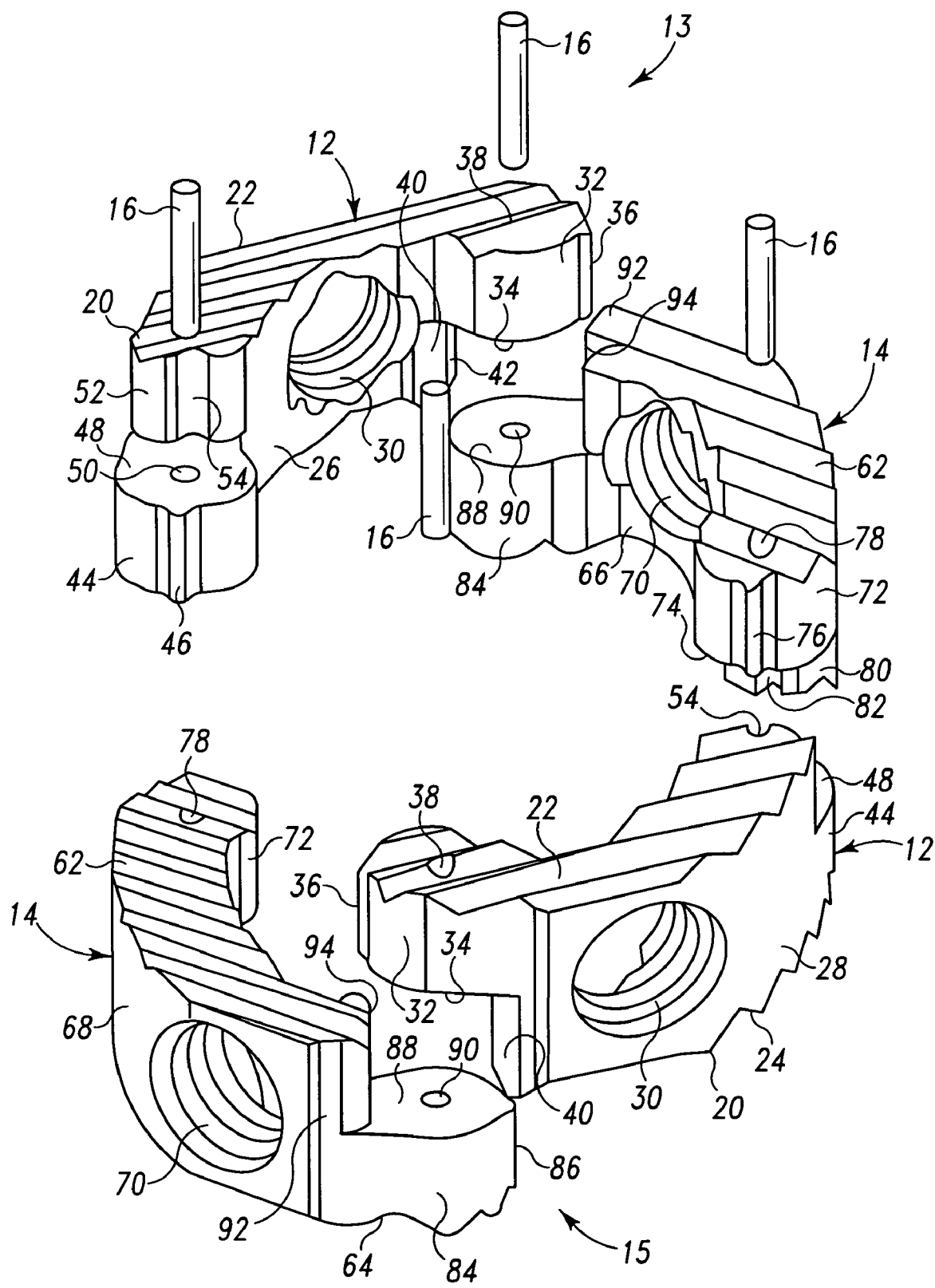
FIG. 2 is an exploded view of the components of the radially expandable spinal interbody device of FIG. 1.
Figure 3:
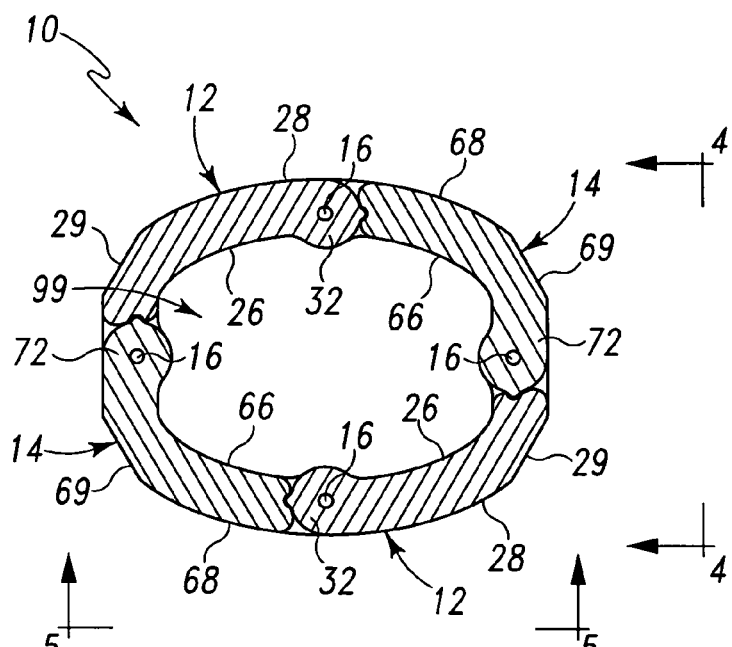
FIG. 3 is a top view of the radially expandable spinal interbody device of FIG. 1.
Figure 4:
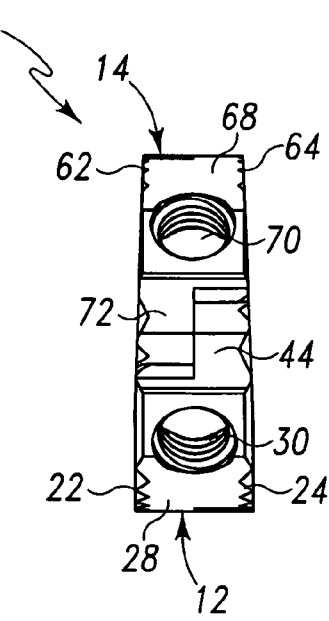
FIG. 4 is a side view of the radially expandable spinal interbody device of FIG. 3 taken along ling 4-4 thereof.
Figure 5:
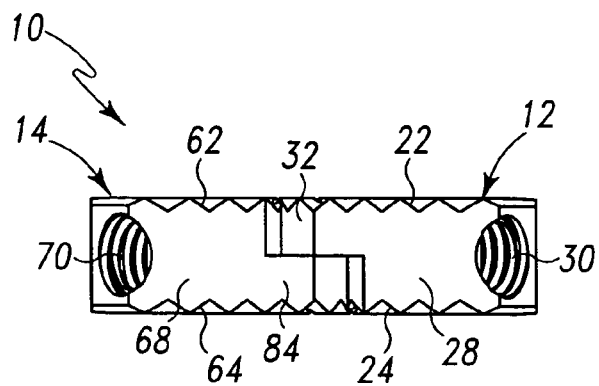
FIG. 5 is a side view of the radially expandable spinal interbody device of FIG. 3 taken along line 5-5 thereof.
Figure 6:
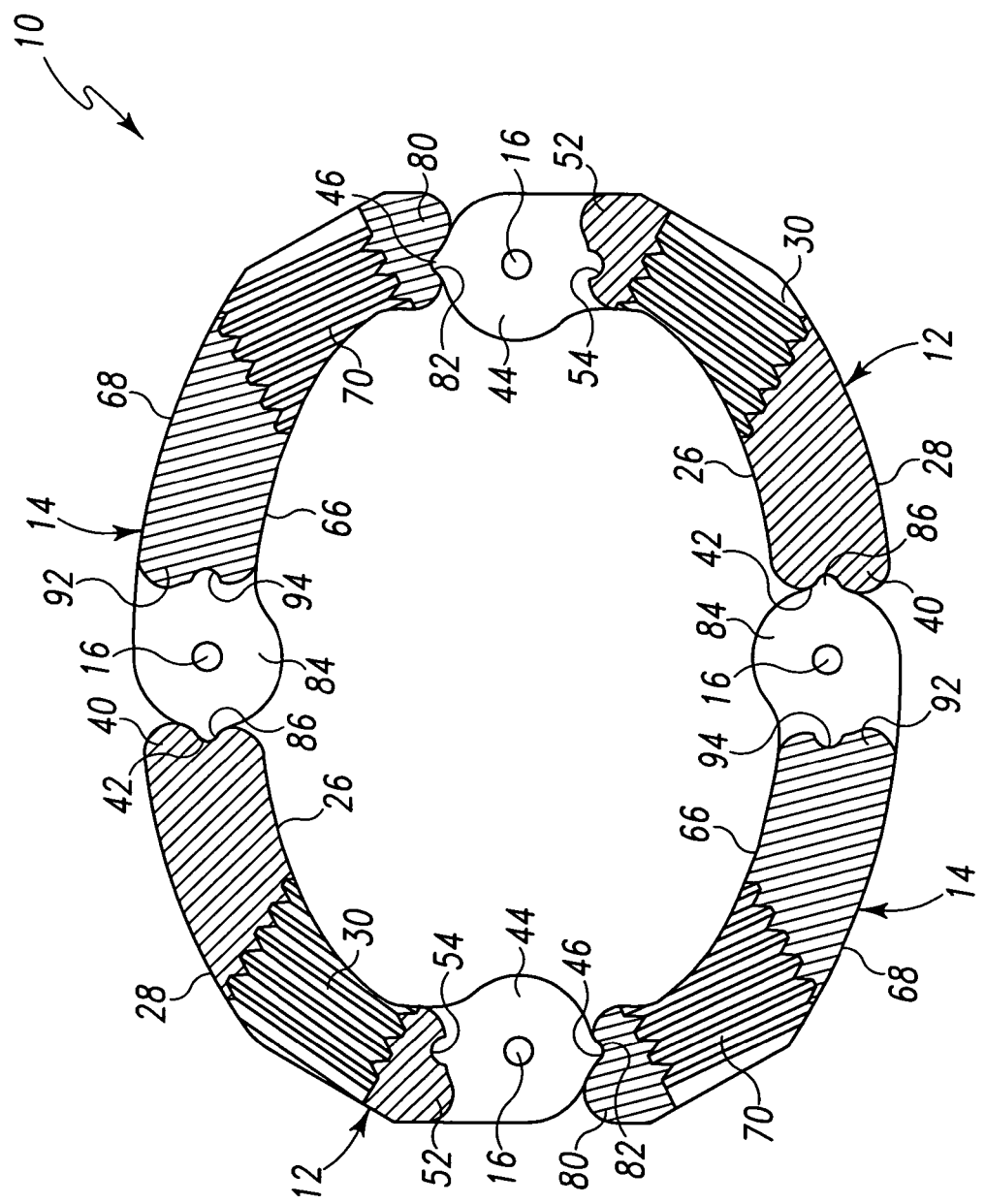
FIG. 6 is a sectional view of the radially expandable spinal interbody device of FIG. 1 taken along line 6-6 thereof.
Figure 8:
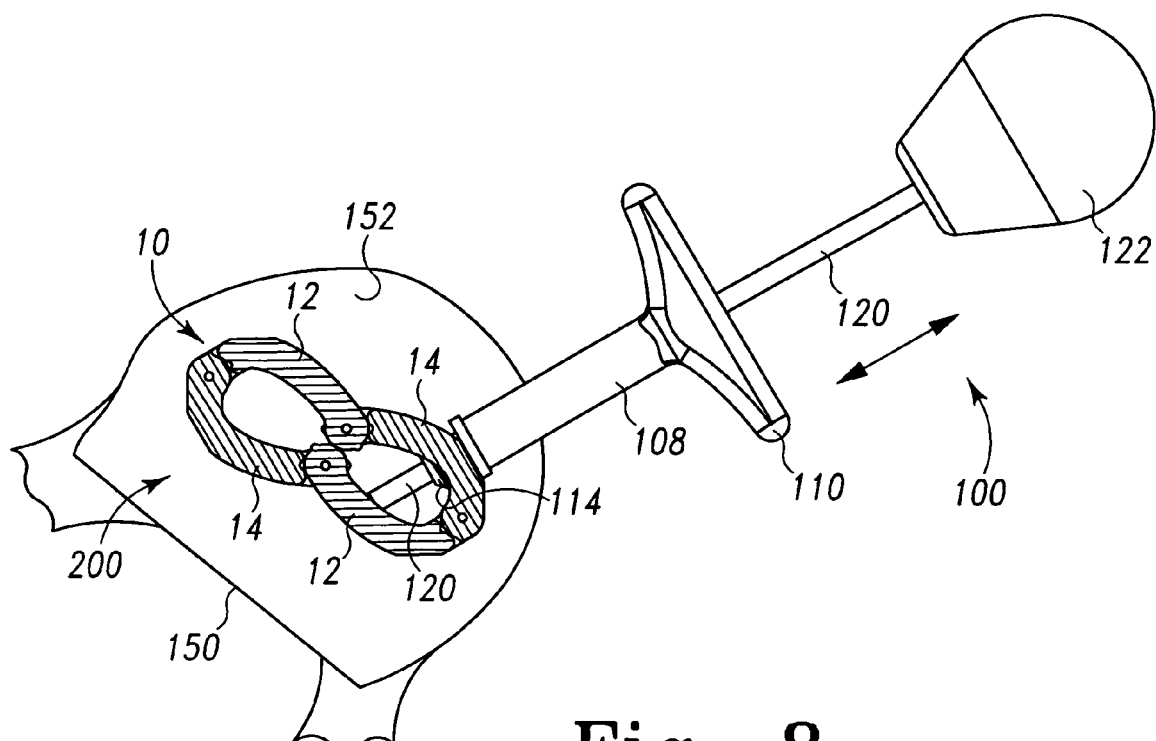
FIG. 8 is an illustration of a stage in a method of use of the radially expandable spinal interbody device of FIG. 1 utilizing the implantation and deployment device of FIG. 7 wherein the radially expandable spinal interbody device is in a pre-expanded or collapsed state adjacent a vertebra.
Figure 9:
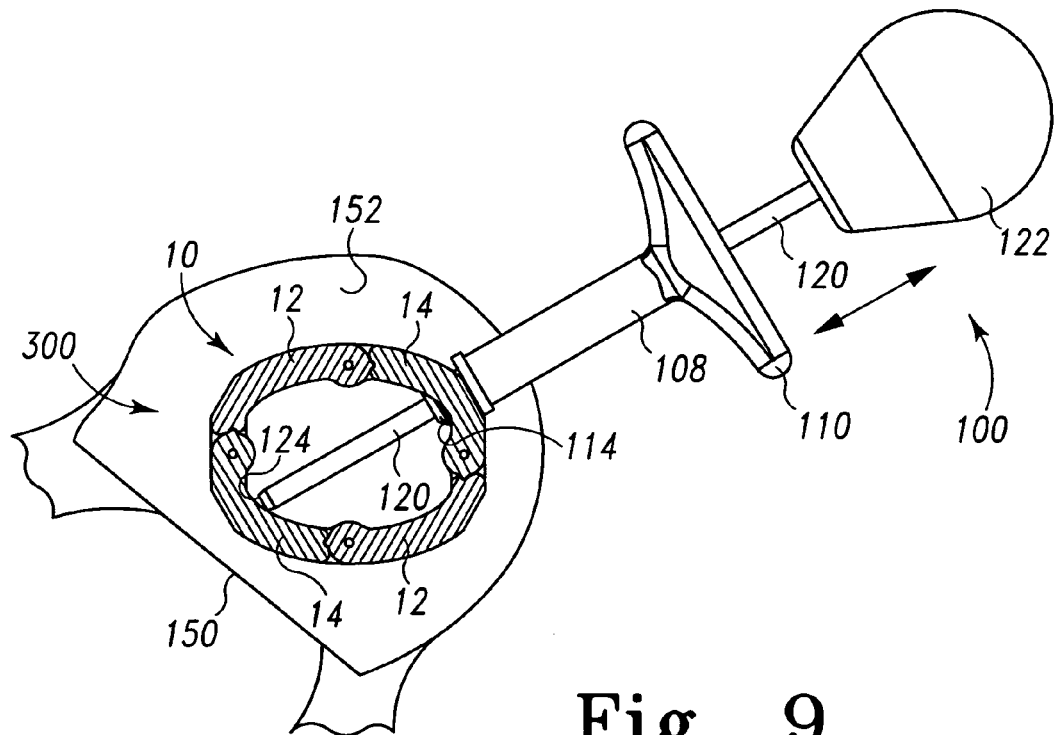
FIG. 9 is an illustration of another stage in the method of use of the radially expandable spinal interbody device of FIG. 1 utilizing the implantation and deployment device of FIG. 7 wherein the radially expandable spinal interbody device is in an expanded or un-collapsed state adjacent the vertebra.

The radially expandable interbody device 10 is defined by a first linkage 13 that is coupled to a second linkage 15. The first linkage 13 is radially pivotally coupled to the second linkage 15 at first ends thereof to define a first radial pivot junction or juncture 17, and at second ends thereof to define a second radial pivot junction or juncture 19. The first linkage 13 is defined by a first pair of links 12 and 14, while the second linkage 15 is defined a second pair of identical links 12 and 14. The first and second links 12 and 14 of the first linkage 13 are radially pivotally connected to one another to define a third radial pivot junction or juncture 21. Likewise, the first and second links 12 and 14 of the second linkage 15 are pivotally connected to one another to define a fourth radial pivot junction or juncture 23. The ends of the first and second linkages 13 and 15 are pivotally connected to one another. In this manner, the linkages 13 and 15 are able to radially collapse in on themselves to a minimum radial size or dimension 200 and radially expand outwardly to a maximum radial dimension or size 300 as defined by a lock mechanism between the links 12, 14 which also provides an overextension feature (lobes with a pocket on one end thereof and a projection on the other end thereof). As best seen in FIG. 8, the curvature and pivoting of the connected links 12 and 14 of the first and second linkages 13 and 15, when collapsed, defines a "FIG. 8" or minimum radial dimension (see, e.g. FIG. 8). As best seen in FIG. 3, the curvature of the connected links 12 and 14 of the first and second linkages 11 and 13, when expanded, defines an ovoid interior 99 that defines a maximum radial dimension of the radially expandable interbody device 10. This shape approximates the end anatomy of a spinal disc (see, e.g., FIG. 9). The links 12 and 14 are joined via hinge or pivot pins 16 (see, e.g. FIG. 2) made of an appropriate biocompatible material. The hinge pins 16 may provide reference markers on the interbody device and as such would be made from a marker-distinctive material (a radio opaque material) such as tantalum. Other materials may be used.

The first link 12 is defined by a generally curved body 20 having a serrated or toothed upper surface 22 and a serrated or toothed lower surface 24. The upper and lower serrations 22 and 24 are directional (see, e.g., FIGS. 1, 2 and 3). The body 20 defines an inner curved surface 26 and an outer curved surface 28. A multi-directional threaded bore 30 is provided in the body 20. The longitudinal axis of the bore 30 is essentially perpendicular to the arc of the body 20. In order to provide connectivity at one end of the body 20 of the link 12 to another link (i.e. link 14), the body 20 has an upper hinge or flange 32 on one end thereof. The upper hinge 32 is generally rounded, defines an undersurface 34, and has an axial bore 38 extending from the upper surface 22 through the upper hinge 32 to the lower surface 24. As best seen in FIG. 2, the upper hinge 32 has a ridge or projection 36 that extends axially along the upper hinge 32. When assembled, the ridge 36 of the first link 12 co-acts with a channel, or groove or pocket 94 in the end 92 of lobes of the second link 14 to provide a lock mechanism to prevent the device from over opening or extending. The body 20 also has an end surface 40 that is below the lower surface 34 of the upper hinge 32. The end surface 40 has an axial groove, channel or pocket 42 of lobes thereof. The groove 42 co-acts with a ridge 86 of a lower hinge 84 of the second link 14 that again provides a lock mechanism to prevent the device from over opening or over extending.

In order to provide connectivity at another end of the body 20 of the link 12 to another link (i.e. link 14), the body 20 has a lower hinge or flange 44 on another end thereof. The lower hinge 44 is generally rounded, defines an upper surface 48, and has an axial bore 50 extending from the upper surface 48 through the lower hinge 44 to the lower surface 24. As best seen in FIG. 2, the lower hinge 44 has a ridge or projection 46 that extends axially along the lower hinge 44. When assembled, the ridge 46 of the lower hinge 44 of the first link 12 co-acts with a channel, groove or pocket 82 of lobes in the end 80 of the second link 14 to provide a lock mechanism to prevent the device from over opening or over extending. The body 20 also has an end surface 52 that is above the upper surface 48 of the lower hinge 44. The end surface 52 has an axial groove, channel or pocket 54 of lobes thereof. The groove 54 co-acts with a ridge 76 of an upper hinge 72 of the second link 14 that again provides a lock mechanism to prevent the device from over opening or over extending.

The second link 14 is defined by a generally curved body 60 having a serrated or toothed upper surface 62 and a serrated or toothed lower surface 64. The upper and lower serrations 62 and 64 are directional (see, e.g., FIGS. 1, 2 and 3). The body 60 defines an inner curved surface 66 and an outer curved surface 68. A multi-directional threaded bore 70 is provided in the body 60. The longitudinal axis of the bore 70 is essentially perpendicular to the arc of the body 60. In order to provide connectivity at one end of the body 60 of the link 14 to another link (i.e. link 12), the body 60 has an upper hinge or flange 72 on one end thereof. The upper hinge 72 is generally rounded, defines an undersurface 74, and has an axial bore 78 extending from the upper surface 62 through the upper hinge 72 to the lower surface 74. As best seen in FIG. 2, the upper hinge 72 has a ridge or projection 76 that extends axially along the upper hinge 72. When assembled, the ridge 76 of the second link 14 co-acts with the channel, groove or pocket 54 of lobes in the end 52 of the second link 12 to provide a lock mechanism to prevent the device from over opening or over extending. The body 60 also has an end surface 80 that is below the lower surface 74 of the upper hinge 72. The end surface 80 has an axial groove, channel or pocket 82 of lobes thereof. The groove 82 co-acts with the ridge 46 of the lower hinge 44 of the first link 12 that again provides a lock mechanism to prevent the device from over opening or over extending.

In order to provide connectivity at another end of the body 60 of the link 14 to another link (i.e. link 12), the body 60 has a lower hinge or flange 84 on another end thereof. The lower hinge 84 is generally rounded, defines an upper surface 88, and has an axial bore 90 extending from the upper surface 88 through the lower hinge 84 to the lower surface 64. As best seen in FIG. 2, the lower hinge 84 has a ridge or projection 86 that extends axially along the lower hinge 84. When assembled, the ridge 86 of the lower hinge 84 of the second link 14 co-acts with a channel, groove or pocket 42 of lobes thereof in the end 40 of the first link 12 to provide a lock mechanism to prevent the device from over opening or over extending. The body 60 also has an end surface 92 that is above the upper surface 88 of the lower hinge 84. The end surface 92 has an axial groove, channel or pocket 94 of lobes thereof. The groove 94 co-acts with the ridge 36 of the upper hinge 32 of the first link 12 that again provides a lock mechanism to prevent the device from over opening or over extending.

As depicted in FIG. 2, the links 12 and 14 are pivotally connected to one another via the hinge or pivot pins 16 that extend into the respective hinge bores of the links 12, 14. The first linkage 11 includes a first link 12 that is pivotally connected to a second link 14. Particularly, the upper hinge 32 of the first link 12 is disposed over the lower hinge 84 of the second link 14 such as to align bores 38 and 90 of the upper and lower hinges 32, 84 respectively. A pivot pin 16 is then provided in the bores 38, 90. The second linkage 13 also includes a first link 12 that is pivotally connected to a second link 14. Particularly, the upper hinge 32 of the first link 12 is disposed over the lower hinge 84 of the second link 14 such as to align bores 38 and 90 of the upper and lower hinges 32, 84 respectively. A pivot pin 16 is then provided in the bores 38, 90. As well, the first and second linkages 11, 13 are pivotally connected to one another and at both ends thereof. Particularly, the upper hinge 72 of the second link 14 of the second linkage 13 is situated over the lower hinge 44 of the first link 12 of the first linkage 11 such that the respective bores 78 and 50 are aligned. A pivot pin 16 is then provided in the bores 78, 50. The upper hinge 72 of the second link 14 of the first linkage 11 is situated over the lower hinge 44 of the first link 12 of the second linkage 13 such that the respective bores 78 and 50 are aligned. A pivot pin 16 is then provided in the bores, 78, 50. The serrations or teeth of the links are oriented to provide directional gripping during implantation and use. Particularly, the serrations of the links are oriented essentially radially when the interbody device is expanded (see, e.g., FIG. 3).

The various hinge ridges or projections of the links 12, 14 and end grooves or channels of the links 12, 14 provide various features/functions for the radially expandable interbody device 10. In one form, the hinge ridges and end groove form expansion stops for the radially expandable interbody device 10 and particularly for each link relative to other links. An expansion stop is formed by a hinge projection of one link and an end groove of another link. In the collapsed state as in FIG. 8, the links 12, 14 of the interbody device 10 are oriented such that hinge projections of one link and adjacent end grooves of an adjacent link do not register and thus are free to pivot relative to one another. When the radially expandable interbody device 10 is expanded (see, e.g., FIG. 9), the links 12, 14 pivot such that the hinge projections of one link and adjacent end grooves of an adjacent link do register thus providing a pivot locking mechanism at a maximum expansion of the links. This provides over extension prevention.

The version of the interbody device as shown in the figures has four (4) segments or links that form the body thereof. It should be appreciated, however, that the interbody device may be fashioned from additional or more than four segments or links. Thus, the interbody device may be formed of a body having up to n segments or links.

Figure 7:
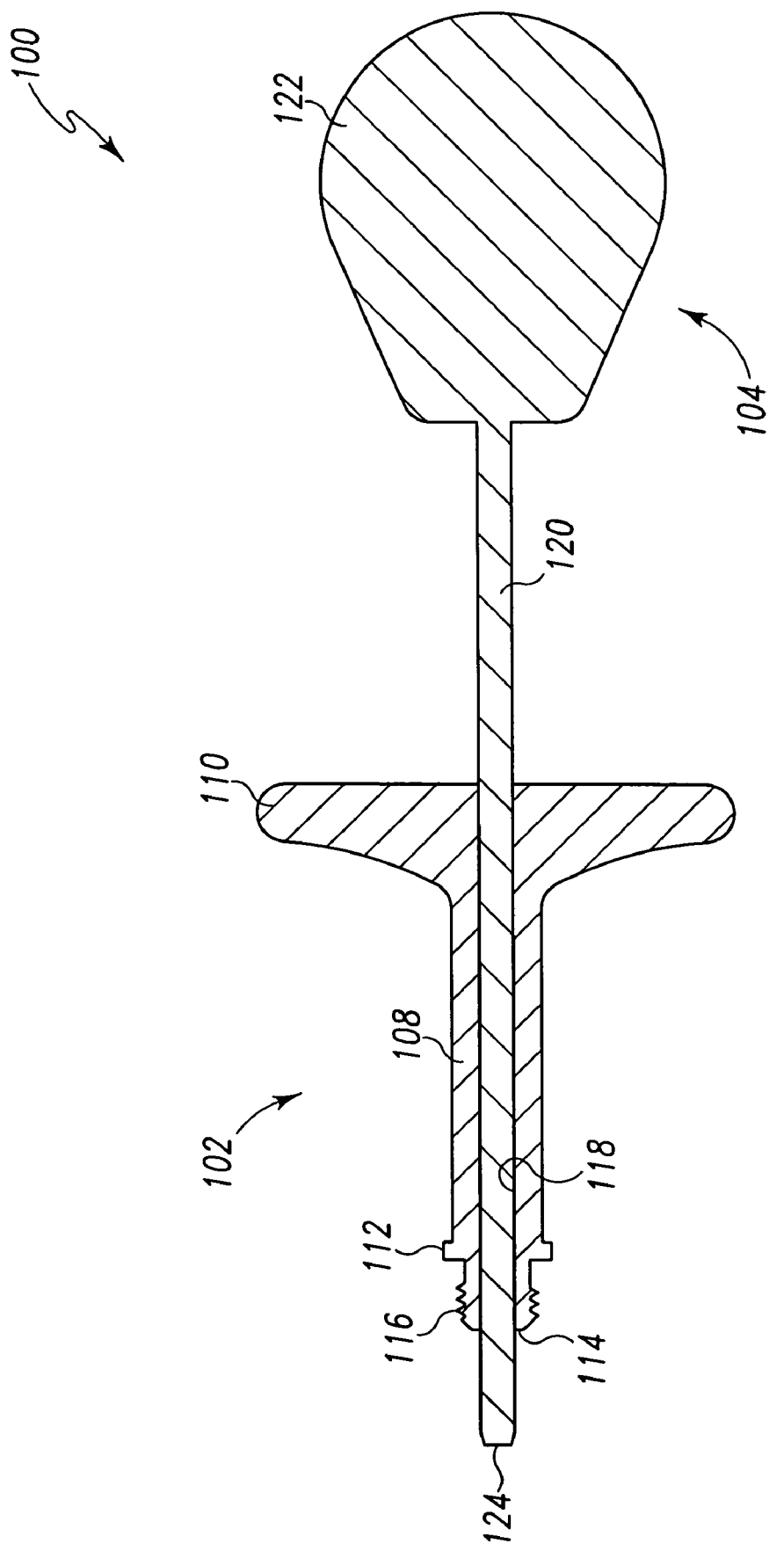
FIG. 7 is a sectional view of an implantation and deployment device for use with the radially expandable spinal interbody device of FIG. 1.

FIG. 7 depicts a surgical tool 100 that may be used with and/or for the implantation and deployment of the radially expandable interbody device 10. Particularly, the surgical tool 100 is used for various implantation functions such as reaming of an implant site, deploying the radially expandable interbody device 10, and the insertion of bone graft, allograft or BMP within the radially expandable interbody device 10. The surgical tool 100 is fashioned from an appropriate biocompatible material such as one or more of those described above. The surgical tool 100 includes a positioning portion 102 and a deploy portion 104. The positioning portion 102 is defined by a cylindrical body or shaft 108 having a handle 110 formed at one end of the shaft 108 and a tapered end 114 formed at another end of the shaft 108 distal the handle 110. External threads 116 are formed on the end 114. These threads are sized to correspond to the threaded bores 30 and 70 of the links 12 and 14 respectively of the interbody device 10. In this manner, the positioning tool 102 may be threadedly coupled to the interbody device 10 during implantation and orientation. (see, e.g. FIGS. 8 and 9). The shaft 108 has a bore 118 that extends from the end 114 to and through the handle 110.

The deploy portion 104 is defined by a rod 120 extending from a grip 122. The rod 120 is dimensioned to be received in the shaft bore 118 and extend axially therefrom. The rod 120 has a tapered end 124 at an end of the rod 120 distal the grip 122. The grip 122 forms a handle that is essentially bulb-shaped. The deploy portion 104 is thus configured to axially move back and forth relative to the positioning portion 102. When the positioning tool 102 is attached to the radially expandable interbody device 10 and the interbody device 10 has been appropriately placed at an implant site (see, e.g., FIGS. 8 and 9), axial movement of the deploy portion 104 expands the radially expandable interbody device 10 as shown in an unexpanded state in FIG. 8, to the expanded radially expandable interbody device 10 as shown in an expanded state in FIG. 9.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A spinal interbody device comprising:
   a first curved linkage having a first end and a second end, the first and second ends each having a first end surface and a second end surface recessed from the first end surface, each first end surface having a ridge and each second end surface having a groove; and
   a second curved linkage having a first end and a second end, the first and second ends each having a first end surface and a second end surface recessed from the first end surface, each first end surface having a ridge and each second end surface having a groove;
   the first end of the first curved linkage and the first end of the second curved linkage pivotally coupled to one another at a first pivot junction defining a first pivot axis and the second end of the first curved linkage and the second end of the second curved linkage pivotally coupled to one another at a second pivot junction defining a second pivot axis to define movement between a collapsed position of the spinal interbody device whereby the first and second curved linkages have a first radial dimension and an expanded position of the spinal interbody device wherein the first and second curved linkages have a second radial dimension that is greater than the first radial dimension;
   wherein the ridge on the first end surface on the first end of the first curved linkage and the groove on the second end surface on the first end of the second curved linkage extend co-axial with the first pivot axis and co-act to inhibit the expansion of the first curved linkage relative to the second linkage;
   wherein the groove on the second end surface on the second end of the first linkage and the ridge on the first end surface on the second end of the second curved linkage extend co-axial with the second axis and co-act to inhibit the expansion of the first linkage relative to the second linkage.

2. The spinal interbody device of claim 1, wherein:
   the first pivot junction includes a first radio opaque pivot pin forming a first marker; and
   the second pivot junction includes a second radio opaque pivot pin forming a second marker.

3. The spinal interbody device of claim 1, wherein the second radial dimension anatomically mimics a vertebral face.

4. The spinal interbody device of claim 1, wherein:
   the first curved linkage includes an upper hinge flange at the first pivot junction and a lower hinge flange at the second pivot junction;
   the second curved linkage includes a lower hinge flange at the first pivot junction and an upper hinge flange at the second pivot junction;
   the upper hinge flange of the first curved linkage is coupled to the lower hinge flange of the second linkage by a first pin at the first pivot junction; and
   the lower hinge flange of the first curved linkage is coupled to the upper hinge flange of the first linkage by a second pin at the second pivot junction.

5. The spinal interbody device of claim 1, wherein:
   the first curved linkage comprises a first link pivotally coupled to a second link at a third pivot junction;
   the second curved linkage comprises a third link pivotally coupled to a fourth link at a fourth pivot junction;
   each of the first, second, third, and fourth links includes a body, an upper hinge flange extending from an end of the body, and a lower hinge flange extending from an opposite end of the body;
   the upper hinge flange of the first link pivotally coupled to the lower hinge flange of the third link at the first pivot junction;
   the lower hinge flange of the first link is pivotally coupled to the upper hinge flange of the second link at the third pivot junction;
   the upper hinge flange of the second link pivotally coupled to the lower hinge flange of the fourth link at the second pivot junction;
   the upper hinge of the fourth link is coupled to the lower hinge flange of the third link at the fourth pivot junction.

6. The spinal interbody device of claim 5, wherein:
   the third pivot junction includes a third radio opaque pivot pin forming a third marker; and
   the fourth pivot junction includes a fourth radio opaque pivot pin forming a fourth marker.

7. The spinal interbody device of claim 5, wherein the first and third links are identical and the second and fourth links are identical.

8. The spinal interbody device of claim 5, wherein the first, second, third and fourth links each include a threaded bore extending from an exterior surface to an interior surface of each respective link.

9. The spinal interbody device of claim 1, wherein:
the first curved linkage comprises a first link pivotally coupled to a second link defining a third pivot axis at a third pivot junction,
the first link providing the first end of the first curved linkage and having a third end, the third end having a first end surface and a second end surface recessed from the first end surface, the first end surface of the third end having a ridge and the second end surface of the third end having a groove;
the second link providing the second end of the first curved linkage and having a fourth end, the fourth end having a first end surface and a second end surface recessed from the first end surface, the first end surface of the fourth end having a ridge and the second end surface of the fourth end having a groove;
the ridge on the first end surface on the third end of the first link and the groove on the second end surface on the fourth end of the second link extend co-axial with the third pivot axis and are configured to co-act to inhibit the expansion of the first link relative to the second link;
the second curved linkage comprises a third link pivotally coupled to a fourth link defining a fourth pivot axis at a fourth pivot junction,
the third link providing the first end of the second curved linkage and having a fifth end, the fifth end having a first end surface and a second end surface recessed from the first end surface, the first end surface of the fifth end having a ridge and the second end surface of the fifth end having a groove;
the fourth link providing the second end of the second curved linkage and having a sixth end, the sixth end having a first end surface and a second end surface recessed from the first end surface, the first end surface of the sixth end having a ridge and the second end surface of the sixth end having a groove;
the ridge on the first end surface on the fifth end of the third link and the groove on the second end surface on the sixth end of the fourth link extend co-axial with the fourth pivot axis and are configured to co-act to inhibit the expansion of the third link relative to the fourth link.

10. A spinal interbody device comprising:
a first linkage having a first end and a second end, the first end having a first end surface and a second end surface recessed from the first end surface, the first end surface having a ridge and the second end surface having a groove; and
a second linkage having a first end and a second end, the first end having a first end surface and a second end surface recessed from the first end surface, the first end surface having a ridge and the second end surface having a groove;
the first end of the first linkage and the first end of the second linkage radially pivotally coupled to one another at a first radial pivot junction defining a first pivot axis and the second end of the first linkage and the second end of the second linkage radially pivotally coupled to one another at a second radial pivot junction defining a second pivot axis to define movement between a radially collapsed position of the spinal interbody device whereby the first and second linkages have a first radial dimension and a radially expanded position of the spinal interbody device wherein the first and second linkages have a second radial dimension that is greater than the first radial dimension;
wherein the ridge on the first end surface on the first end of the first linkage and the groove on the second end surface on the first end of the second curved linkage extend parallel to the first pivot axis and engage each other to inhibit over-expansion of the first linkage relative to the second linkage.

11. The spinal interbody device of claim 10, wherein:
the first radial pivot junction includes a first radio opaque pivot pin forming a first marker; and
the second radial pivot junction includes a second radio opaque pivot pin forming a second marker.

12. The spinal interbody device of claim 10, wherein the second radial dimension anatomically mimics a configuration of a vertebral face.

13. The spinal interbody device of claim 10, wherein the first linkage comprises a first link pivotally coupled to a second link defining a third pivot axis at a third pivot junction, and the second linkage comprises a third link pivotally coupled to a fourth link defining a fourth pivot axis at a fourth pivot junction.

14. The spinal interbody device of claim 10, wherein:
the first linkage comprises a first link radially pivotally coupled to a second link at a third radial pivot junction; and
the second linkage comprises a third link radially pivotally coupled to a fourth link at a fourth radial pivot junction;
the first link radially pivotally coupled to the third link at the first radial pivot junction and the second link radially pivotally coupled to the fourth link at the second radial pivot junction.

15. The spinal interbody device of claim 14, wherein:
the first radial pivot junction includes a first radio opaque pivot pin forming a first marker;
the second radial pivot junction includes a second radio opaque pivot pin forming a second marker;
the third radial pivot junction includes a third radio opaque pivot pin forming a third marker; and
the fourth radial pivot junction includes a fourth radio opaque pivot pin forming a fourth marker.

16. The spinal interbody device of claim 14, wherein the first and third links are identical and the second and fourth links are identical.

17. The spinal interbody device of claim 10, wherein:
the first linkage includes a lower hinge flange extending from a portion of the first end and an upper hinge flange extending from a portion of the second end;
the second linkage includes an upper hinge flange extending from a portion of the first end and a lower hinge flange extending from a portion of the second end;
the lower hinge flange on the first linkage pivotally coupled to the upper hinge flange on the second linkage by a first pin and the upper hinge flange on the first linkage pivotally coupled to the lower hinge flange on the second linkage by a second pin.

18. A kit for the implantation of a spinal interbody device into an intervertebral space, the kit comprising:
a spinal interbody device comprising:
a first curved linkage having a first end, a second end, and a first threaded bore, the first end having a first end surface and a second end surface recessed from the first end surface, the first end surface having a ridge and the second end surface having a groove;
a second curved linkage having a first end, a second end, and a second threaded bore, the first end having a first end surface and a second end surface recessed from the first end surface, the first end surface having a ridge and the second end surface having a groove;

the first end of the first linkage and the first end of the second linkage radially pivotally coupled to one another along a first pivot axis at a first radial pivot junction and the second end of the first linkage and the second end of the second linkage radially pivotally coupled to one another along a second pivot axis at a second radial pivot junction to define a radially collapsed position of the spinal interbody device whereby the first and second curved linkages have a first radial dimension and a radially expanded position of the spinal interbody device wherein the first and second curved linkages have a second radial dimension that is greater than the first radial dimension;

wherein the ridge on the first end surface on the first end of the first curved linkage and the groove on the second end surface on the first end of the second curved linkage extend parallel to the first pivot axis and engage each other to inhibit the movement of the first linkage relative to the second linkage; and a tool configured to implant the spinal interbody device into an intervertebral space via one of the first and second threaded bores when the spinal interbody device is in the radially collapsed position, and to deploy the spinal interbody device into the radially expanded position when the spinal interbody device has been implanted into the intervertebral space.

19. The kit for the implantation of a spinal interbody device into an intervertebral space of claim 18, wherein:

the first curved linkage comprises a first curved link radially pivotally coupled to a second curved link at a third radial pivot junction; and the second curved linkage comprises a third curved link radially pivotally coupled to a fourth curved link at a fourth radial pivot junction;

the first curved link radially pivotally coupled to the third curved link at the first radial pivot junction and the second curved link radially pivotally coupled to the fourth curved link at the second radial pivot junction.

* * * * *